United States Patent [19]

Daub et al.

[11] Patent Number: 5,091,538

[45] Date of Patent: Feb. 25, 1992

[54] DICYANOVINYLSUBSTITUTED FURAN DERIVATIVES

[75] Inventors: Jörg Daub, Regensburg; Knut M. Rapp, Offstein; Petra Seitz, Straubing; Rainer Wild, Obrigheim; Josef Salbeck, Regensburg, all of Fed. Rep. of Germany

[73] Assignee: Suddeutsche Zucker-Aktiengesellschaft, Mannheim, Fed. Rep. of Germany

[21] Appl. No.: 445,092

[22] Filed: Dec. 5, 1989

Related U.S. Application Data

[63] Continuation-in-part of Ser. No. 195,754, May 19, 1988, abandoned.

[30] Foreign Application Priority Data

Jun. 5, 1987 [DE] Fed. Rep. of Germany ....... 3718917

[51] Int. Cl.[5] .................. C07D 405/12; C07D 307/42; C07D 307/45; C07D 307/54
[52] U.S. Cl. .................... 546/283; 549/214; 549/218; 549/497; 549/499; 549/502; 549/472
[58] Field of Search ............. 549/472, 487, 499, 214, 549/218, 502; 546/283; 548/161, 222, 327, 517

[56] References Cited

FOREIGN PATENT DOCUMENTS 0293651 12/1988 European Pat. Off. ............ 549/472

OTHER PUBLICATIONS

Chemiker-Zeitung 96, 535 (1972).
Chem. Abstr. 105, 78 849 q (1986).
"Chemie in unserer Zeit" 9, 85 (1975).
Kirk-Othmer, Encyclopedia of Chemical Technology 3. Ed. vol. 6, 122 (1979).
Chem. Abstr. 102, 299 304z, (1985).
Chem. Abstr. 103, 79 543 f (1985).
Angew. Chem. 96, 980 (1984).
Angew. Chem. 88, 311 (1976).
Kirk-Othmer, Encyl. of Chemical Technology 3. Ed. vol. 7, 359, 362 (1979).

J. Amer. Chem. Soc. 106, 7626 (1984).
Angew. Chem. 90, 927 (1978).

(List continued on next page.)

Primary Examiner—Alan L. Rotman
Attorney, Agent, or Firm—Armstrong, Nikaido, Marmelstein, Kubovcik & Murray

[57] ABSTRACT

The present invention refers to dicyanovinylsubstituted furan derivatives, processes for their production and their application. The new furan derivatives are represented by the general formula

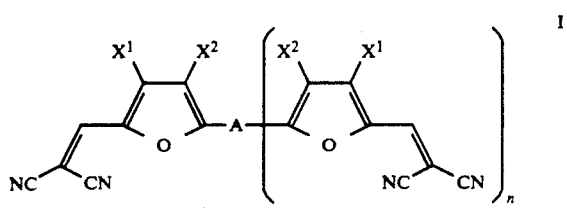

wherein $x^1$ and $x^2$ are equal or different and stand for H, alkyl, alkenyl, aryl, halogen, $NO_2$ or CN.

In the general formula I, n may be 0 or 1. In case of n=0, A means e.g. $-CH_2OR^1$ (with e.g. $R^1$=H, alkyl or aryl).

The compounds according to this invention can be used directly or in the form of their cycloadducts in several applications of electro-optical fields, e.g. for the manufacture of optical data recording systems or organic (electron) conducting materials or electron-transfer catalysts.

1 Claim, 4 Drawing Sheets

OTHER PUBLICATIONS

Kirk-Othmer, Encyl. of Chemical Technology 3. Ed. vol. 6, 124 (1979).
Carbohydr. Res. 155, 99 (1986).
J. March, Advanced Organic Chemistry 3. Ed., 1985 J. Wiley & Sons, Inc., New York, pp. 796-798.
Synthesis 1976, 133.
Chemiker-Zeitung 96, 535 (1972).
Chem. Abstr. 105, 78 849 q (1986).
"Chemie in unserer Zeit" 9, 85 (1975).
Kirk-Othmer, Encyclopedia of Chemical Technology 3. Ed. vol. 6, 122 (1979).
Chem. Abstr. 102, 299 304z, (1985).
Chem. Abstr. 103, 79 543 f (1985).
Angew. Chem. 96, 980 (1984).
Angew. Chem. 88, 311 (1976).
Kirk-Othmer, Encyl. of Chemical Technology 3. Ed. vol. 7, 359, 362 (1979).
J. Amer. Chem. Soc. 106, 7626 (1984).
Angew. Chem. 90, 927 (1978).
Kirk-Othmer, Encycl. of Chemical Technology 3. Ed. vol. 6, 124 (1979).
Carbohydr. Res. 155, 99 (1986).
J. March, Advanced Organic Chemistry 3. Ed., 1985 J. Wiley & Sons, Inc., New York, pp. 796-798.
Synthesis 1976, 133.

DICYANOVINYLSUBSTITUTED FURAN DERIVATIVES

This application is a continuation-in-part of application Ser. No. 195,754 filed May 19, 1988.

Dicyanovinyl substituted furan derivatives, process for obtaining them and their applications.

The present invention refers to novel furan derivatives according to the general formula I shown in claim 1, which, as a result of their properties, are suited in a special way among others for electro-optical applications.

Compounds, which are capable of producing a dye-stuff and therefore an image, by light-absorption, without any developing or washing processes, can be utilized in optical informational recording- or processing systems. Because it is possible with these substances to make grain-free layers, very great storage densities are reachable (Chemiker-Zeitung 96, 535 (1972)).

Spiropyranes as those like formula 1

(comp. JP 61 18 782 (86 18 782); Chem. Abstr. 105, 78 849 q (1986)) belong to substances, which can be changed by UV-exposure to coloured compounds and which can be discoloured by heat influence.

The applications and advantages of reversible photochromic substances are described in "Chemie in unserer Zeit" 9, 85 (1975), namely the high optical resolution (high storage density), the control of exposure during the "writing", and the possibility of erasure or changing of parts of a picture.

In Kirk-Othmer, Encyclopedia of chemical technology 3. Ed. Vol. 6, 122 (1979) are mentioned as disadvantages of organic photochromic materials: small spectral shifts, slow reversal times, fatigue, or any combination of the three.

As class of substances, where a valence tautomerism is responsible for the chromogenic behaviour spiropyranes and fulgides are mentioned. The former can be partly built in a polymer by co-polymerisation with a suitable monomer. Fulgide belong also to the more intensely studied photochromic systems (comp. e.g. Chem. Abstr. 102, 229 304z (1985), GB 2 142 011 cited in Chem. Abstr. 103, 79 543 f (1985) with compounds of formula 2).

In Angew. Chem. 96, 980 (1984) a system is described, in which a dihydroazulene derivative via light absorption is transformed in a coloured heptafulvene derivative which cyclizes by heat treatment again to the dihydroazulene. In contrast to R=NO$_2$ the system 3 A⇌3 B is chemically stable for R=OCH$_3$, i.e. an at least 15-fold fore- and backreaction doesn't change the extinction coefficient. No side reactions or irreversible degradation takes place.

The above described photochromic system is synthesized according to the following reaction sequence:

8-Methoxyheptafulvene is accessible in two steps and good yield starting from cyclooctatetraene. A disadvantage of the applied p-anisaldehyde (R=OCH₃) is the absence of a functional group, which would allow to connect the photochromic product in a suitable manner e.g. covalently to polymers.

Surprisingly advantageous however is the utilization of 5-hydroxymethylfurfuraldehyde (in the following called HMF) with formula 4 instead of anisaldehyde for the following reasons:

1. The electronic influence of a furan ring on bound substituents is comparable with this of an O-alkylbenzene ring, i.e., that furfuraldehyde reacts similarly as anisaldehyde (p-methoxybenzaldehyde).

2. The hydroxymethyl group in HMF enables, as additional functional group, a coupling to an oligo- or polymer. Such a bonding is mentioned clearly as an advantage in the case of spiropyranes ( Kirk-Othmer, Encyclopedia of chemical technology 3. Ed. Vol. 6, 122 (1979). A derivatization at the hydroxymethyl group allows also a systematic control of the solubility.

3. Typical carbonyl reactions allow too, through a condensation with amines and a following oxidation of the hydroxymethyl group to the aldehydic state, to prepare e.g. compounds with formula 5, which are obtained via Knoevenagel-reaction with malononitrile.

4. The possibility to "build" different bridges between two furans, allows a perturbation of the dicyanovinyl groups and so a variation of the electron acceptor ability or of the di- or polyeneophilic properties.

5. 5-Hydroxymethylfurfuraldehyde has as starting component additionally the great advantage to be prepared in a single reaction step from renewable raw material (carbohydrate) and moreover on large-scale with water as sole solvent. Especially, the utilization of agricultural, (occasionally) on surplus produced carbohydrates e.g. sucrose, in technical fields via the intermediate HMF shows the advantage of the inventive dicyanovinylsubstituted furans.

6. Another surprising advantage of furylidenemalononitriles compared with phenylanaloga is e.g. the full reversibility of the reduction of compound 6, as shown by cyclovoltammatry. Compound 7 is under the same conditions not reversibly reducible. This is also to see in connection with the substituent effect mentioned in 1.

This means, that the compound 6 similar to tetracyanoquinodimethane (TCNQ) (formula 8)

which can be reversibly reduced also in a twofold one-electron reaction, can be used as component of so-called "organic metals", or an electron-storage system or electron-transfer-catalyst.

The spectroelectrochemistry of 6 shows reversible electrochromic behaviour. An application in displays is possible because of the good reversibility of the electron absorption.

A combination of photochromic and electrochromic behavior is observed with the cycloadduct of compound 6 with 8-methoxyheptafulvene ($CH_3OH$ is eliminated) prepared in Example 4. The different electrochemical reactivities of the dihydroazulene form 13A and the heptafulvene form 13B make the cycloadduct useful in opto-electronic devices.

When compound 13A (in solution) is exposed to light, it is converted into 13B. The reverse reaction of 13B to 13A is so fast at ambient temperature that a change in color is not observed. If there is a potential difference of $-1050$ mV (vs. ferrocene as the standard) between a transparent electrode containing a solution of the cycloadduct and a counter-electrode, an electron transition takes place and current will flow, when form 13B is generated by exposure to pulses of light. When the exposure to the light pulses is ended, the current ceases to flow.

A cell of the type described above is suitable for use in information processing because a sequence of light pulses can be converted into a sequence of current pulses. It is also suitable for use in modulating an electric current by variable light irradiation (photomodulation of an electric current by light). It can also be used as "light switch", since a unit (machine, lamp or the like) can be switched on or off by a light pulse after its conversion into an electric pulse by means of a appropriate electronic circuit.

Figure 1A:
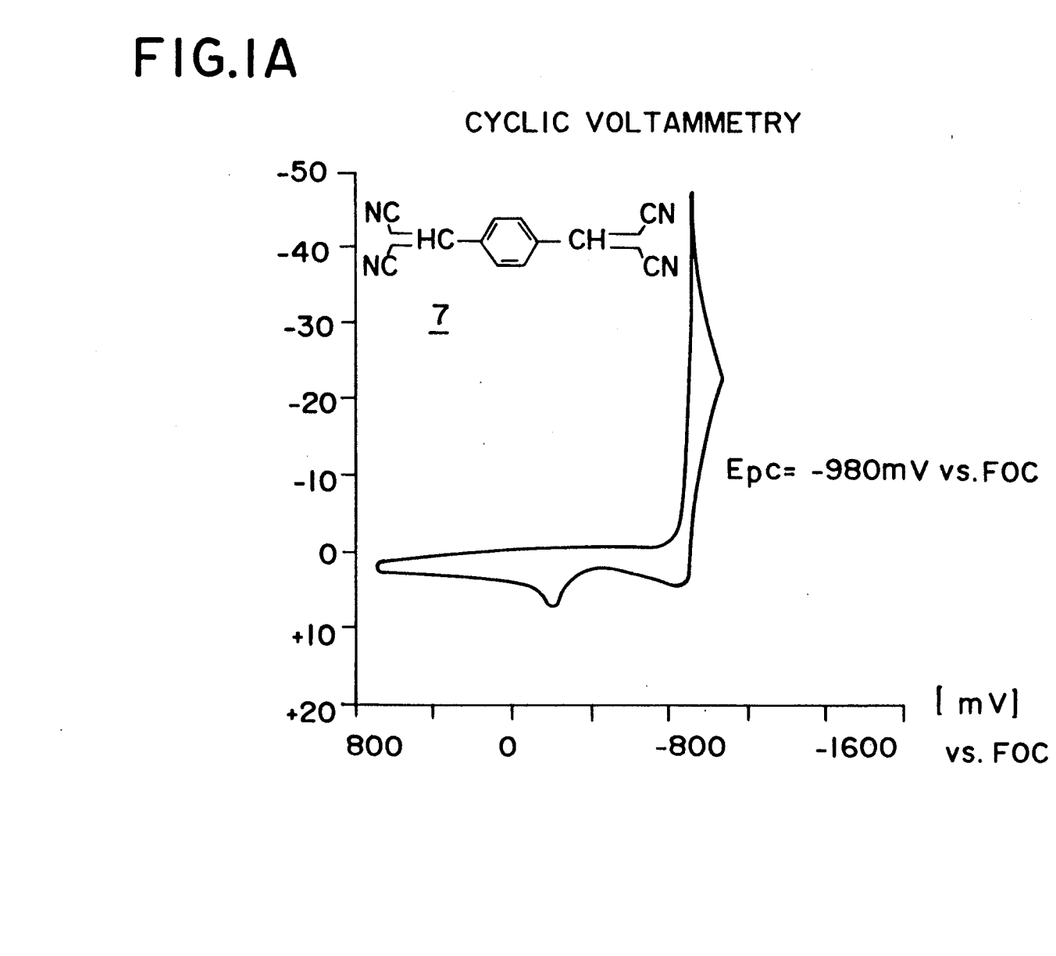
Figure 1B:
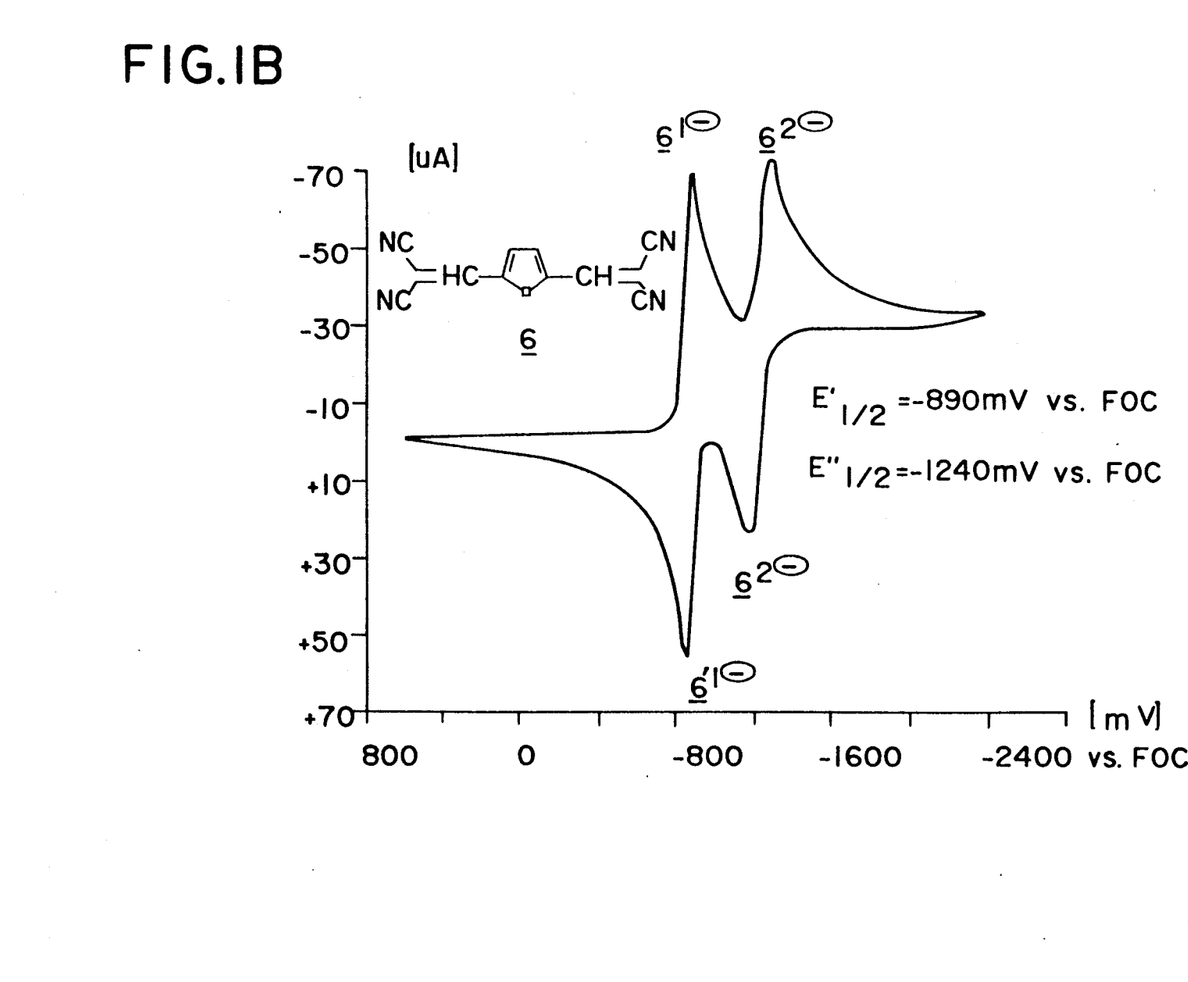
Figure 2A:
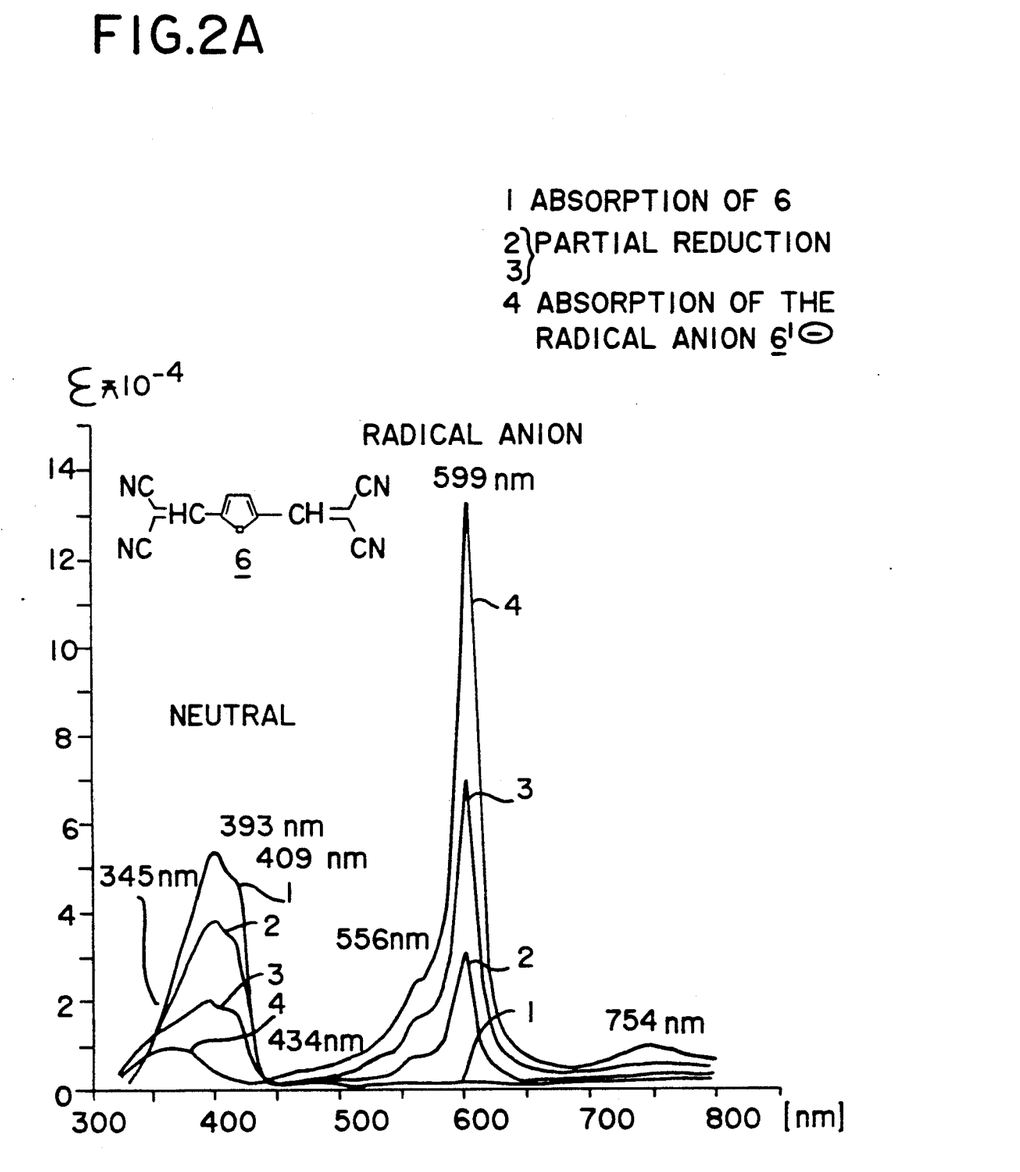
Figure 2B:
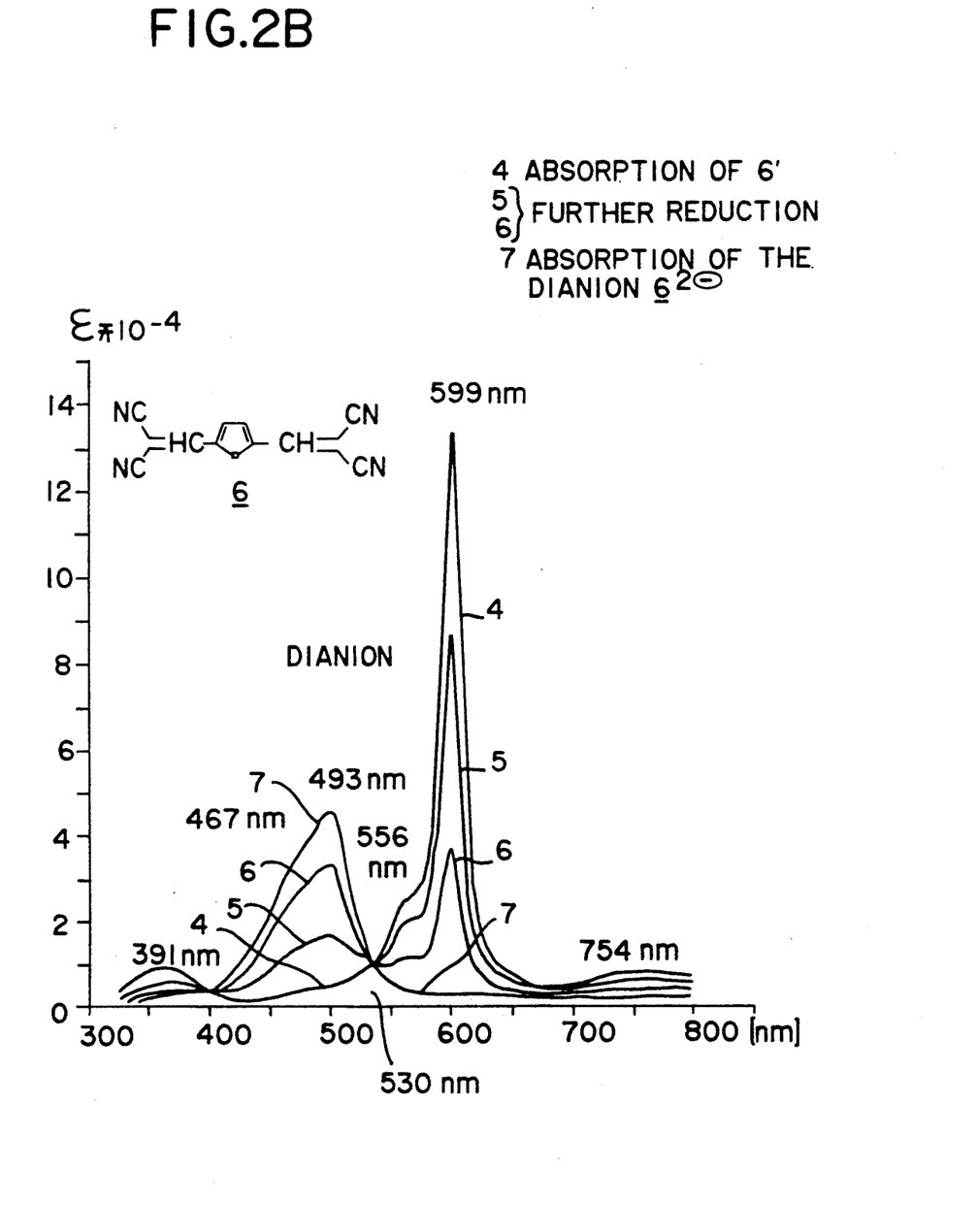

Details due to the reduction of 6, as determined by cyclovoltammetry under aprotic conditions under formation of $6^{-}$, respectively $6^{2-}$ as well as to the absorption spectrum of the radical anion and the dianion formed and obtained by spectroelectrochemistry are shown in FIG. 1 and 2. Radical anion $6^{-}$ displays a rather narrow absorption band at $\lambda=599$ nm (dark blue solution) with a high extinction coefficient. Thus, contrarily to the radical anion $8^{-}$ of TCNQ with an absorption at $\lambda=840$ nm, radical anion $6^{-}$ absorbs in the visible part of the spectrum.

The reversible reducibility of alkylidene malononitriles is mentioned in Angew. Chem. 88, 311 (1976). The formation of radical anions of tetracyanoethylene or TCNQ is also described in Kirk-Othmer, Encyclopedia of chemical technology 3. Ed. Vol. 7, 359, 362 (1979).

A correlation between reversible redox properties (electrochemistry) and chromogenic features (photochemistry) appears too in the long-known class of fulgides. Thus, in J. Amer. Chem. Soc. 106, 7626 (1984) is described, that the reversible generated radical anion of formula 9 reacts in an electro-cyclic reaction to a structure similar to the ring-closed, photochemically produced of chromogenic fulgides.

In Angew. Chem. 90, 927 (1978) tetracyano compounds are mentioned among others too, and applications of these two-step redox systems as redox indicators, electron acceptors, catalyst for electron transfer, light-sensitive systems and electron conducting materials are mentioned.

The furylidenmalononitriles described in this invention can therefore be characterized as important new substance class for electro-optical applications.

7. An advantage of furanic substituents at the dihydroazulene residue is also the rapid back-reaction of the coloured heptafulvene structure after light exposure, which is favoured in addition to electron withdrawing substituents for A, e.g. $A=A^1=CH=C(CN)_2$, $NO_2$. A slow back-reaction is mentioned in Kirk-Othmer, Encyclopidia of chemical technology 3. Ed. Vol. 6, 124 (1979), as an explicit disadvantage of organic photochronic materials. For a fast optical information-storing and -processing, furylidenmalononitrile-derivatives, analogous to 5 , meet ideal preconditions.

8. Another advantage of the dihydroazulene-heptafulvene-systems $3A \rightleftarrows 3B$ ($R=OCH_3$) is also the relatively great shift from about 380 nm to about 470 nm with a simultaneous increase of the extinction coefficient. Processes for producing 3- and/or 4-substituted HMF-derivatives are described e.g. in Carbohydr. Res. 155, 99 (1986), where via the oxidation of 1,2; 4,5-diisopropylidenfructose followed by a Grignard-reaction und dehydratisation several 3-substituted HMF-derivatives are synthesized e.g. formula 10

-continued
R = Me, Ph, CH$_2$—CH=CH$_2$

Other substituents can be introduced in the furan ring according to the rules of the chemistry of aromatic compounds. The 3- or 4-substituted HMF-derivatives are further reacted as the unsubstituted HMF.

The preparation of compounds with n=0 and A=A$_1$=CH$_2$OR$^1$ is achieved by an etherification or esterification e.g. with acetic anhydride of HMF followed by a Knoevenagel-condensation.

For A = A$_1$ = one starts from HMF and a suitable ortho-disubstituted phenyl derivative and makes first the aminal or O, N- or S, N-acetal, which is oxidized in one step e.g. with BaMnO$_4$ to the aromatic (e.g. Benzimidazol) and at the same time to the aldehydic stage (from the hydroxymethyl group).

The crossed benzoin addition with HMF or derivatives thereof as e.g. 5-acetoxymethylfurfuraldehyde followed by oxidation leads to compounds e.g. of formula 11

11

The oxidation of the deacetylated compound and Knoevenagel-condensation with malononitrile yields compounds according to formula

12

General manufacturing method for n=1 and A=A$_2$=—CH=N—Z—N=CH—:

The diamino compound is dissolved in a suitable solvent optionally as hydrochloride or a similar salt, e.g. hydrazine hydrochloride or -hydrogensulfate in water or ethylenediamine, 1,12-diaminododecane or p-phenylenediamine in methylene chloride. To the stirred solution two mol equivalents of HMF, is dropped slowly at room temperature dissolved in a suitable solvent, e.g. water or methylene chloride.

Either a solid precipitates in a short time, which is optionally recrystallized but also can be used often directly in the following oxidation step, or it has to be heated for the formation of the Schiff base and/or water removing agents had to be added. The conditions for the formation of Schiff bases are described e.g. in J. March, Advanced Organic Chemistry 3. Ed., 1985 J. Wiley & Sons, Inc., New York, S. 796-798.

The oxidation of the both hydroxymethyl groups in these amine-HMF-condensation products can be achieved e.g. with active manganese dioxide or barium manganate. In contrast to the literature, Synthesis 1976, 133, where it is started that azines are unstable in the presence of manganese dioxide, the oxidation of the HMF-azine is possible. In the inventive process other oxidants (besides the mentioned manganese compounds), which are able to oxidize hydroxymethyl groups to the aldehydic stage, are not excluded. Thin layer chromatographically the oxidation progress can be followed. The oxidation can be made in benzene, toluene or trichloroethane eventually with concomitant azeotropic destillative removing of the reaction water.

The obtained dialdehydes are reacted with malononitrile according the common procedures, optionally with TiCl$_4$ catalysis, and the dicyanovinylsubstituted furan derivatives are received as good crystallizing solids.

Examples of compounds with n=0 A=A$_1$=CH$_2$OR$^1$:

R$^1$=H, methyl, ethyl, n-propyl, i-propyl, n-butyl, t-butyl, octyl, phenyl, p-hydroxyphenyl, p-nitrophenyl, p-dimethylaminophenyl, 2-pyridyl, 1-naphtyl, 2-naphtyl, trimethylsilyl, triphenylsilyl, acetyl, palmitoyl, benzoyl, p-nitrobenzoyl, p-dimethylaminobenzoyl, methansulfonyl, p-toluenesulfonyl, phosphonyl (di-sodium salt), 2-methoxyethyl, 4-methoxybutyl,

M = Ni, Cu, CO, Ru

A = A$_1$ = CH=N—R$^3$   R$^3$ = methyl, butyl, phenyl, p-nitrophenyl, p-dimethylaminophenyl The here mentioned examples should be only illustrative and not restrictive for this invention.

Examples of compounds with n=1 and A=A$_2$=—CH=N—Z—N=CH—:

Z=(single) bond, 1,2-ethanediyl, 1,4-butandiyl, 1,12-dodecanediyl, 1,4-phenyldiyl, 1,3-phenyldiyl, 1,4-naphthalenediyl, 1,5-naphthalenediyl, 1,8-naphthalenediyl, 1,4-(2-nitrophenyl)diyl, 3,5-(1,2,4-triazole) diyl, 2,7-fluorenediyl, 1,4-anthraquinonediyl, 1,5-anthraquinonediyl, 2,6-anthraquinoediyl, 2,6-(4-phenyl-1,3,5-triazine)diyl, 3,6-acridinediyl, 2,6-pyridinediyl, 3,7-(5-phenothiazinium)diylchlorid, 3,8-(5-ethyl-6-phenyl-phenanthridium)diylbromid, M = Ni, Cu, CO, Ru The here mentioned example should be only illustrative and not restrictive for this invention.

EXAMPLE 1

2-(2',2'-dicyanovinyl)-5-acetoxymethyl-furan 1,68 g (10 mmol) 5-acetoxymethylfurfuraldehyde and 0,66 g (10 mmol) malononitrile are dissolved in 50 ml acetonitrile and with 40 mg β-alanine and 10 drops acetic acid are boiled at reflux for 10 h. When cooling the solution, the catalyst precipitates and is filtered off. After concentration one get 2,2 g of lilac-coloured crystals with a melting point of 79° C. Recrystalization from methylene chloride yields colourless crystals with m.p.=80°-82° C.

IR (KBr): 3130, 3100, 3040, 2990, 2940, 2230, 1750, 1610, 1565, 1225, 1195, 1005, 830 cm$^{-1}$ $^1$H-NMR(CDCl$_3$): 7.48 ppm (s), 7.34 ppm (d, 3.7 Hz), 6.67 ppm (d, 3.7 Hz), 5.15 ppm (s), 2.13 ppm (s)

EXAMPLE 2

Bis-5,5'(2'',2''-dicyanovinyl)-furfuraldehyde-azine 12,4 g (50 mmol) HMF-azine are dissolved in 500 ml 1,1,2-trichloroethane with heating and after addition of 115,3 g bariummanganate are boiled at reflux for 7 h. Then the solution is filtered hot and slowly is cooled. Yellow, needle-shaped crystals are formed with m.p.=214° C.

IR (KBr): 3140, 3115, 2850, 1670, 1630, 1490, 1410, 1250, 1175, 980, 955, 825, 795 cm$^{-1}$ $^1$H-NMR(DMSO): 9.74 ppm (s,CHO), 8.71 ppm (s), IR (KBr): 3120, 3030, 2220, 1595, 1535, 1380, 1285, 1205, 1197, 1135, 1023, 935, 810, 787, 770 cm$^{-1}$ $^1$H-NMR(DMSO): 8.62 ppm, 8.55 ppm, 8.35 ppm, 7.65-7.25 ppm $^{13}$C-NMR(DMSO): Signals of the predominantly present rotamer
154.0 ppm, 150.8 ppm, 150.0 ppm, 143.7 ppm, 125.7 ppm, 120.4 ppm, 114.2 ppm, 112.9 ppm, 77.9 ppm.

EXAMPLE 3

Bis 5-((2',2'-dicyanovinyl)-furfuryl)-ether 4,70 g (20 mmol) Bis (5-formyl-furfuryl)-ether are dissolved in 150 ml toluene and 2,64 g (40 mmol) malononitrile are added. Together with 50 mg β-alanine and 200 mg acetic acid the mixture is boiled at reflux for 4 h and is slowly cooled. The solids formed are filtered off and washed with toluene. Yield 5,40 g, m.p.: 148° C. (from toluene)

IR (KBr): 3130, 3045, 2920, 2224, 2212, 1608, 1548, 1494, 1340, 1211, 1194, 1140, 1123, 1029, 974, 798 cm$^{-1}$

NMR (DMSO): 8.26 ppm (s), 7.42 ppm (d, 3.65 Hz), 6.87 ppm (d, 3.65 Hz), 4.71 ppm (s)

EXAMPLE 4

Reaction of 2,2'-(2,5-furandiyldimethylidyne)bis-propanedinitrile with 8-methoxyheptafulvene (1:1) in dichloromethane.

To a fresh prepared, N$_2$-saturated solution of 650 mg (4.45 mmol) 8-methoxyheptafulvene in 30 ml absolute dichloromethane are added 980 mg (4.80 mmol) 2,2'-(2,5-furandiyldimethylidyne)bis-propandinitrile and about 10 mg hydroquinone and the mixture is stirred at room temperature for 18 h, excluding air with a mercury valve. The progress of the reaction is monitored by thin layer chromatography. After the cycloadducts had be formed, the formerly deep red solution turns transparent brown. The solvent is evaporated, the remaining brown oil dissolved in ether, filtered, the solvent in vacuo evaporated and the residue is dried in high vacuum. One gets a brownish solid. By columne chromatography over silica gel, with dichloromethane/petrol ether 2:1 as eluent, one obtains an orange solid with m.p. 172°-173° C. in a 52% yield. MS(70 eV): m/e=322(100%, M$^+$), 295 (31%, M-HCN)

IR(KBr) : 3120, 3050, 2240, 1605, 1573, 1475, 1280, 1045, 820, 710 cm$^{-1}$ 7.68 ppm (d, 3.7 Hz), 7.38 ppm (d, 3.7 Hz) 2,44 g (10 mmol) dialdehyde and 1,32 g (20 mmol) malononitrile are dissolved in 150 ml acetonitrile and after addition of 40 mg β-alanine and 100 mg acetic acid are heated at reflux for 4 h. By slow cooling crystals are formed, which are filtered off and rinsed with cold solvent. m. p.: 238°-242° C.

UV/VIS(CH$_3$CN): $\lambda_{max}$.(lgε)=250 (4.4), 327 (3.7), 443 nm (4.6)

$^1$H-NMR(250MHz,CDCl$_3$) δ=3.81 (m;1H,H-8a),5.81 (dd,J=
10.4 Hz,3.8 Hz;1H,H-8), 6.32-6.38 (m;1H,H-7), 6.52-6.65 (m;3H,H-4,H-5 H-6),
7.09 (d,J=4.0 Hz;1H,furan-H), 7.12

(s;1H,H-3), 7.30 (d,J=4.0 Hz; 1H,-furan-H), 7.46ppm(s;1H,propanedinitril-H)

EXAMPLE 5

Reaction of 2,2'-(2,5-furandiyldimethylidyne)bis-propanedinitrile with 8-methoxyheptafulvene (1:2) in dichloromethane.

To a fresh prapared, $N_2$-saturated solution of 1.80 g (13 mmol) 8-methoxyheptafulvene in 100 ml absolute dichloromethane are added 850 mg (3.86 mmol) 2,2'(2,5-furandiyldimethylidyne) bis-propanedinitrile and ca. 10 mg hydroquinone and the mixture is stirred at room temperature for 1 day excluding air with a mercury valve. The progress of the reaction is monitored by thin layer chromatography. After termination of the cycloaddition the formerly deep red solution turns to transparent brown. The solvent is evaporated, the remaining brown oil is dissolved in ether, filtered, the solvent in vacuo evaporated and the residue is dried in high vacuo. A brownish solid is obtained.

Methanol elimination from the formed tetrahydroazulene.

To a vigourously stirred solution of the formed tetrahydroazulene in 150 ml absolute benzene 20 g $P_2O_5$ and 2.8 g potassiumcarbonate are added and the solution is boiled at reflux for 6 h. After termination of the reaction the mixture is filtered through a Büchner funnel filled with sand and silica gel. The filtrate is concentrated in vacuo to a yellow-brown oil.

Via chromatography on silica gel with dichloromethane/petrolether (1:1) an orange solid is obtained in a 44% yield and with m.p.: 182°–184° C.

MS(70eV): m/e=424(100%,M+), 397(11%,M-HCN), 370(11%,M-2HCN)

IR(KBr): 1040, 780, 760, 698 cm$^{-1}$

UV/VIS(CH$_3$CN): $\lambda_{max}$.(lgε)=218(4.2), 245(4.2), 294(3.8),

354(4.0,s), 433,6(4.5), 456 nm(4.4)

$^1$H-NMR(250MHz,CDCl$_3$) δ=3.78(m,2H,H-8a,H-8a'), 5.83(dd,

J=10.2 Hz,3.8 Hz;2H,H-8,H-8'), 6.29–6.37 (m;2H,H-7,H-7'), 6.40(d,J=6.0 Hz;2H, H-4,H-4'), 6.46–6.83(m;4H,H-6,H-6', H-5,H-5'), 6.86(s;2H,H-3,H-3'), 7.02 (s;2H,furan-H)

EXAMPLE 6 AND BRIEF DESCRIPTION OF DRAWINGS 1-A, 1-B, 2A AND 2B

The electro-optical behaviour of 2,2'-(2,5-furandiyldimethylidyne)bis-propanedinitrile.

The reduction of 2,2'-(2,5-furandiyldimethylidyne)-bis-propane-dinitrile (compound 6) yields a radical anion and then a dianion $6^{2-}$, which is, in contrast to the terephtal-derivative 7, fully reversible transformed to the neutral compound. This is shown in FIGS. 1A and 1B respectively (cyclic voltammetry in acetonitrile, 0,1 n tetrabutylammonium hexafluorophosphate).

The optical properties of 6, the radical anion $6^{·-}$ and the dianion $6^{2-}$ are shown in FIG. 2. The neutral compound 6 has a light-yellow colour, according to an absorption at 393 nm (absorption 1), the radical anion $6^{·-}$ is deep blue, and the exceptionally narrow absorption at 599 nm is shown as curve 4 in FIG. 2A.

Further reduction yields the dianion $6^{2-}$, which has an orange colour (absorption maximum at 493 nm, curve 7 in FIG. 2B). The conditions of the reduction are as follows: acetonitrile, 0,1 n tetrabutyl ammonium hexafluorophosphate reduction to $6^{·-}$ at −1000 mV vs. ferrocene, reduction to $6^{2-}$ at −1500 mV vs. ferrocene.

We claim:

1. A dicyanovinylsubstituted furan compound of the formula wherein A$_1$ is CH$_2$OR$^1$, and wherein R$^1$ is H or a C$_1$–C$_8$ alkyl, phenyl, p-hydroxyphenyl, p-nitrophenyl, p-dimethylamino phenyl, naphthyl, 2-pyridyl, trimethylsilyl, triphenylsilyl, acetyl, palmitoyl, benzoyl, p-nitrobenzoyl, methanesulfonyl, p-toluenesulfonyl, phosphonyl, 2-methoxyethyl or 4-methoxybutyl group.

* * * * *